United States Patent
Gottenbos et al.

(10) Patent No.: US 11,284,706 B2
(45) Date of Patent: Mar. 29, 2022

(54) METHOD AND SYSTEM FOR ORAL PH CHANGE

(71) Applicant: KONINKLIJKE PHILIPS N.V., Eindhoven (NL)

(72) Inventors: Bart Gottenbos, Budel (NL); Alwin Rogier Martijn Verschueren, 'S-Hertogenbosch (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 154 days.

(21) Appl. No.: 15/536,431

(22) PCT Filed: Dec. 11, 2015

(86) PCT No.: PCT/EP2015/079332
§ 371 (c)(1),
(2) Date: Jun. 15, 2017

(87) PCT Pub. No.: WO2016/102201
PCT Pub. Date: Jun. 30, 2016

(65) Prior Publication Data
US 2017/0347787 A1   Dec. 7, 2017

(30) Foreign Application Priority Data
Dec. 23, 2014 (EP) .................... 14200070

(51) Int. Cl.
*A46B 11/00* (2006.01)
*A46B 15/00* (2006.01)
(Continued)

(52) U.S. Cl.
CPC .............. *A46B 11/002* (2013.01); *A46B 7/04* (2013.01); *A46B 15/0024* (2013.01);
(Continued)

(58) Field of Classification Search
CPC . A46B 15/0024; A61C 17/227; A61C 19/063; A61C 19/066
See application file for complete search history.

(56) References Cited

U.S. PATENT DOCUMENTS 3,148,684 A * 9/1964 Keeler ............... A46B 11/0003
401/140
3,335,443 A * 8/1967 Parisi et al. ........... A61C 17/20
15/167.1
(Continued)

FOREIGN PATENT DOCUMENTS

EP   0748342 B1   10/2001
EP   1444975 A2   8/2004
(Continued)

*Primary Examiner* — Edward Moran

(57) ABSTRACT

A new method and a system for increasing the pH of a composition applied on teeth and/or gums. The composition is gelable under the influence of a pH change. The device includes a dispensing unit for the composition, a distal end of which is adapted to apply the composition onto teeth or gums. The device further includes an electrode system having first and second electrodes, the first electrode adapted to be held against the composition at a location at or near teeth or gums, and the second electrode adapted to be held against the composition at a location away from teeth or gums. The electrode system is adapted so as to provide an electrical potential difference of 1.5 to 10 Volt between the first and second electrodes.

14 Claims, 2 Drawing Sheets

(51) Int. Cl.
  *A61C 15/04* (2006.01)
  *A61C 17/16* (2006.01)
  *A61C 19/06* (2006.01)
  *A46B 7/04* (2006.01)
  *A61K 8/73* (2006.01)
  *A61C 1/02* (2006.01)
  *C25B 9/00* (2021.01)

(52) U.S. Cl.
  CPC ............ *A61C 15/047* (2013.01); *A61C 17/16* (2013.01); *A61C 19/063* (2013.01); *A61K 8/733* (2013.01); *A61K 8/736* (2013.01); *C25B 9/00* (2013.01); *A46B 2200/1066* (2013.01); *A46B 2200/20* (2013.01); *A61C 1/02* (2013.01)

(56) References Cited

U.S. PATENT DOCUMENTS

| | | | | |
|---|---|---|---|---|
| 4,969,868 | A | * | 11/1990 | Wang ................ A46B 15/0002 15/167.1 |
| 6,344,488 | B1 | * | 2/2002 | Chenite ................ A61K 9/0019 514/777 |
| 2004/0258723 | A1 | | 12/2004 | Singh et al. |
| 2006/0275225 | A1 | | 12/2006 | Prencipe et al. |
| 2007/0154363 | A1 | | 7/2007 | Joshi et al. |
| 2007/0212665 | A1 | | 9/2007 | Jimenez et al. |
| 2008/0280248 | A1 | * | 11/2008 | Pitts ...................... A61B 5/053 433/32 |
| 2011/0123958 | A1 | | 5/2011 | Piergallini et al. |
| 2011/0135379 | A1 | | 6/2011 | Jimenez et al. |
| 2012/0251971 | A1 | * | 10/2012 | Fish .................. A46B 15/0002 433/27 |

FOREIGN PATENT DOCUMENTS

| | | |
|---|---|---|
| JP | 2005205068 A | 8/2005 |
| JP | 2012179211 A | 9/2012 |
| JP | 2013141601 A | 7/2013 |
| WO | 2007087350 A2 | 8/2007 |
| WO | 2008135957 A2 | 11/2008 |
| WO | 2011068774 A2 | 6/2011 |
| WO | 2011077299 A1 | 6/2011 |
| WO | 2013116618 A1 | 8/2013 |
| WO | 2014056824 A2 | 4/2014 |

\* cited by examiner

METHOD AND SYSTEM FOR ORAL PH CHANGE

CROSS-REFERENCE TO PRIOR APPLICATIONS

This application is the U.S. National Phase application under 35 U.S.C. § 371 of International Application No. PCT/EP2015/079332, filed on Dec. 11, 2015, which claims the benefit of European Patent Application No. 14200070.2, filed on Dec. 23, 2014. These applications are hereby incorporated by reference herein.

FIELD OF THE INVENTION

The invention is in the field of oral care, and pertains to a system and a method for the administration of pH-sensitive oral care agents. Notably, the invention pertains to the in situ solidification of polymeric gels.

BACKGROUND OF THE INVENTION

The human oral cavity, notably teeth and gums, is generally in need of oral care agents. Think of, e.g., antiplaque agents, anti-tartar agents, anti-gingivitis agents, anti-bacterial agents, and others.

Such agents are generally administered from toothpastes and/or oral rinse liquids. Due to the typical environment of the oral cavity, e.g. having saliva present, a standard difficulty in the art is that active agents from toothpastes and oral rinses are quickly reducing in concentration after their application. Therefore they cannot protect the mouth for long times, and they need therefore to be applied several times daily.

WO 2008/135957 discloses a method for cleaning dental plaque biofilm from teeth wherein a liquid gelable composition is applied to the teeth. From the composition a gel layer is produced, wherein the gel layer adheres more strongly to the dental plaque bio film than the bio film adheres to the teeth. Ultimately the gel layer is removed from the teeth, and the dental plaque biofilm along therewith, as the dental plaque biofilm adheres to the gel layer.

These liquids, for example, are chitosan solutions, that are viscous fluids which can easily flow in for example interproximal spaces, or below the gum line. Chitosan solutions can form strong adhesive gels when mixed with alkaline solutions to increase the overall pH in the chitosan solution. Such gels can be maintained unobtrusively for long times in secluded spaces, such as the interproximal space.

The in situ formation of the gel can be realized by first administering a gelable liquid (e.g. based on chitosan), and then administering a second liquid (e.g. a sodium hydroxide solution) to bring about gelation. However, inducing increased pH with a second alkaline solution has certain drawbacks. E.g., having to take in a second solution can be an inconvenience to users, thus reducing compliance. Also, due to its alkalinity, the solution will be prone to being considered unpleasant to the user, and safety issues could impart its use. Also, mixing a second solution is not very effective in achieving a quick pH increase.

It would therefore be desirable to provide a more convenient method to bring about an in situ increase of pH after the administration of the gelable composition. Particularly, it would be desired to provide a non-invasive method that can be conducted by operating a device, rather than by delivering a second solution into the oral cavity.

A similar desire exists in respect of bringing about a pH decrease. This would allow the use of pH-sensitive polymers that gel under influence of a more acidic pH, while being in solution at a higher pH.

A special case of pH responsive gelling would be to use release carriers to bring about gelation, by release of crosslinkers (for example calcium ions for the gelation of alginate or carrageenan solutions). Here, the technology existing in the art relates to particles (e.g. pH-sensitive liposomes, nanoparticles, micelles) that are prompted to release contained active substances at a mild acidic pH (e.g., a pH of 5). In order to apply such pH-sensitive carriers for the release, after administration to the teeth and or gums, of crosslinkers, it would thus be desired to provide a method to bring about an in situ decrease of pH after the administration of an oral care composition comprising an oral care agent, a substance such as alginate or carrageenan that will form a gel under the influence of calcium ions, and a pH-sensitive carrier comprising such calcium ions.

It is therefore an object of the invention to provide a method and a device by which the pH of oral care compositions can be changed, when such compositions have been applied to the teeth and/or gums. Particularly, it is an object of the invention to provide a method and a device for applying an oral care composition that is gelable under the influence of a pH increase, and increasing the pH thereof when such composition has been applied on teeth and/or gums.

SUMMARY OF THE INVENTION

In order to better address the foregoing desires, the invention, in one aspect, provides a device for the application on teeth or gums of an aqueous oral care composition that is gelable under the influence of a change in pH, and changing the pH of said composition when the composition has been applied on teeth or gums; the device comprising a dispensing unit for said composition, a distal end of which is adapted to apply said composition onto teeth or gums, and an electrode system comprising first and second electrodes, the first electrode being adapted to be held against the aqueous liquid composition at a location at or near teeth or gums, and the second electrode being adapted to be held against the aqueous liquid composition at a location away from teeth or gums; the electrode system being adapted so as to provide an electrical potential difference of 1.5 to 10 Volt between the electrodes, such that upon providing said potential difference to the applied composition, hydroxide ions (OH—) form at one electrode, and protons (H+) form at the other electrode, in order to bring about gelation of said composition.

In another aspect, the invention presents a device for the application of an aqueous liquid composition on teeth or gums, whereby the composition is gelable under the influence of a pH increase, the device comprising a dispensing unit for said aqueous liquid substance, a distal end of which is adapted to apply said substance onto teeth or gums, and an electrode system comprising first and second electrodes, the first electrode being adapted to be held against the aqueous liquid substance at a location at or near teeth or gums, and the second electrode being adapted to be held against the aqueous liquid substance at a location away from teeth or gums; the electrode system being adapted so as to provide an electrical potential difference of 1.5 to 10 Volt between the electrodes, such that hydroxide ions (OH—) form at the first electrode, and protons (H+) form at the second electrode.

In yet another aspect, the invention concerns a method of gelling a liquid composition suitable for application on teeth or gums and gelable by increasing the pH thereof, whereby the gelling is conducted by subjecting the liquid composition to an electrical potential difference of 1.5 to 10V when the composition has been applied on teeth or gums.

In a further aspect, the invention presents an oral healthcare kit comprising:

(a) a container having an aqueous liquid oral care composition comprising at least one oral care agent and an aqueous liquid carrier that is gelable under the influence of a pH increase; and (b) an applicator for said composition comprising a dispensing unit for said aqueous liquid oral care composition, a distal end of which is adapted to apply said composition onto teeth or gums, and an electrode system comprising first and second electrodes, the first electrode being adapted to be held against the aqueous composition at a location at or near teeth or gums; and the second electrode being adapted to be held against the aqueous liquid oral care composition at a location away from teeth or gums; the electrode system being adapted so as to provide an electrical potential difference of 1.5 to 10 Volt between the electrodes, such that hydroxide ions (OH—) form at the first electrode, and protons (H+) form at the second electrode.

DETAILED DESCRIPTION OF EMBODIMENTS

Figure 1:
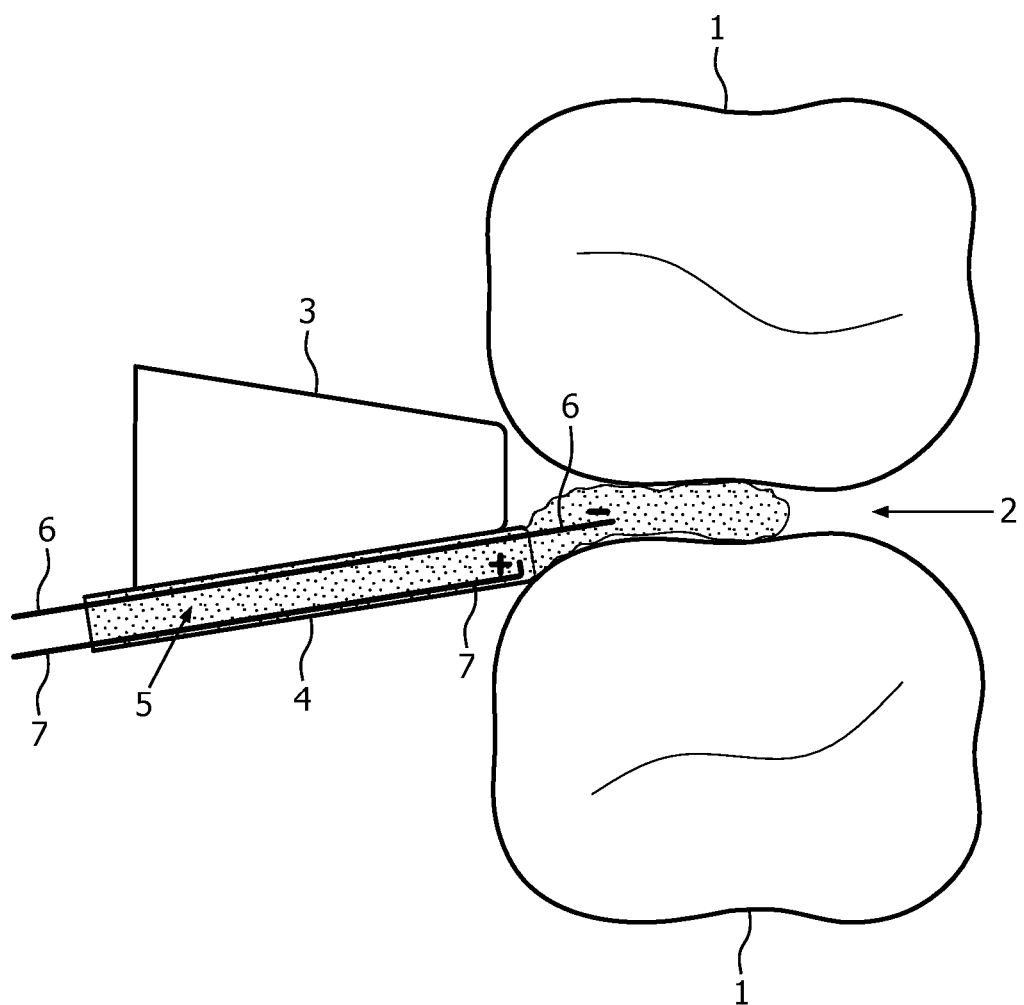
FIG. 1 is a schematic representation of a test using a device according to the invention in applying an oral care composition to teeth.

In a general sense, the invention is based on the judicious insight that the pH of an aqueous liquid composition administered onto teeth or gums, including interproximal spaces, can be changed, i.e. increased or decreased, quickly using electrochemistry. In the event that an electrical potential difference (i.e., a voltage) at or above approximately 1.5 V is applied between two electrodes in an aqueous solution, hydroxide ions (OH⁻) form at the negative electrode (cathode) and protons (H⁺) form at the positive electrode (anode).

According to the invention this principle is advantageously applied to oral healthcare, as it provides, also in the specific environment of the oral cavity, an elegant, and relatively easy way to bring about a pH increase or decrease, without the administration of, respectively, an alkaline or an acidic liquid.

To this end, the invention provides a device for the application of an aqueous oral care composition on teeth or gums, and changing the pH of said composition when the composition has been applied on teeth or gums, the device comprising an electrode system in addition to a dispensing unit for said aqueous liquid substance. The dispensing unit has one end, herein defined as the distal end, that is adapted to apply said composition onto teeth or gums. The device also comprises an electrode system. In the electrode system a first electrode is adapted to be held against the aqueous liquid composition at a location at or near teeth or gums, upon or after application of said composition. A second electrode is adapted to be held against the aqueous liquid composition at a location away from teeth or gums.

The electrode system of the device of the invention has been adapted so as to provide an electrical potential difference of 1.5 to 10 Volt between the electrodes.

To this end, the electrode system is provided with a connection to a suitable electrical power source. Typically, this can be an adapter allowing the electrode system to be connected to a domestic AC outlet, which typically has a voltage such as 230 V or 110 V. Alternatively, this can be a battery or a set of batteries. In one embodiment, the device of the invention comprises a battery compartment having a conductive connection to the electrode system. In another embodiment, the device comprises both an adapter for a domestic AC outlet, and a battery compartment, both of which having a conductive connection to the electrode system.

The dispensing unit is configured such that a distal end thereof is adapted to apply said substance. To this end, the dispensing unit typically comprises a nozzle through which an aqueous liquid composition, such as a gelable aqueous liquid, can be forced outward and be applied onto a desired location in the mouth (hereinafter also indicated as dispensing nozzle). This location will generally be on teeth or on gums, and particularly also in interproximal spaces.

The electrode system comprises first and second electrodes. The first electrode is adapted to be held at or near the aqueous liquid composition at a location at or near teeth or gums. The second electrode is adapted to be held at or near the aqueous liquid composition at a location away from teeth or gums. In the system of the invention, the dispensing unit and either or both of the electrodes can be separate units. Preferably, the electrodes are integrated with the dispensing unit. In that event, it is preferred that the first electrode extends from the distal end of the dispensing unit, i.e. in outward direction (upon usage: into the direction of the teeth or gums). The second electrode can be at any point of the dispensing unit upstream of the first electrode, as long as it can be held against the aqueous liquid substance during or after its application. Thereby the second electrode can be contained in the dispensing unit (e.g. as a metal wire), or it can be part of a wall of the dispensing unit, or itself be a wall of the dispensing unit.

The direction of this electrical potential difference depends on whether the desired pH change is a pH increase or a decrease.

In the event of bringing about a pH increase, the direction of the electrical potential difference is such that hydroxide ions (OH—) form at the first electrode, and protons (H+) form at the second electrode. In that case, the first electrode is the negative electrode. In the event of bringing about a pH decrease, the direction of the electrical potential difference is the reverse, i.e., such that hydroxide ions (OH—) form at the second electrode, and protons (H+) form at the first electrode, which in that case is the positive electrode.

In one embodiment, the device can be set to provide either of the two functions of bringing about a pH increase or decrease. I.e., in this embodiment the device is constructed so as to provide a single direction of the electrical potential difference. This has the advantage that the device can be construed most simply, without necessitating the presence of a switch unit for reversing the direction of the electrical potential difference.

In another embodiment, the device is rendered suitable for providing both a pH increase and a pH decrease, depending on a reversible setting for the electrical potential difference.

In the event of compositions in which the gelation is brought about by the in situ release of crosslinkers, the gelable composition will suitably be provided with pH-sensitive particles comprising such crosslinkers. For example, in this embodiment, the gelable compositions comprise alginate or carrageenan, and the crosslinkers are calcium ions. Preferably, the composition comprises pH sensitive polymers, with functional groups that can be protonized or deprotonized. The gelation then is not based on triggered release of crosslinkers, but just straightforwardly on bringing about a pH increase. An advantage hereof is that many existing compositions can be used that are capable of gelation under the influence of a pH increase, without changing the nature of such compositions. In connection herewith, in a preferred embodiment of the device of the invention, the first electrode is the negative electrode and the second electrode is the positive electrode.

Preferably, the first electrode extends from the distal end of the dispensing unit (i.e. in outward direction, as referred to earlier), and the second electrode is at or near said distal end. This way, the first electrode can be easily held deeper into the mouth, and against any teeth or gums, including interproximal spaces, where it is desired to bring about a pH increase. The position of the second electrode, at or near the distal end of the dispensing unit (e.g., just at or near the exit opening of a nozzle), serves to as much as possible limit the subjection to pH increase to a portion of aqueous gelable liquid that has actually been applied into the oral cavity. If the second electrode were positioned in a direction further upstream then it would be more important to control the duration of applying a voltage, since liquid present in the dispensing unit, downstream of the second electrode, could then start gelling as well, and possibly clog the dispensing unit.

In the event of the administration of a composition that is gelable by a pH increase, it is preferred for the negative electrode to be at a distance of at least 1 mm away from the positive electrode. This serves to prevent the protons formed at the positive electrode from interfering with the gelling to such an extent as decreasing the gelling speed.

Further, the second (positive) electrode is preferably positioned at the dispensing nozzle, or also extending therefrom, yet closer to the dispensing nozzle than the first (negative) electrode. In these embodiments, the generated hydroxide ions are prevented from reaching the dispensing nozzle, as these ions would have to pass a proton rich area around the positive electrode. This prevents any unwanted gelling in or at the nozzle, let alone in the dispensing device.

If, e.g., the positive electrode is at the exit of the dispensing nozzle, the negative electrode will extend at least 1 mm therefrom. For practical reasons, and for the solidity and handling of the device, it is preferred that the negative electrode does not extend to far a distance from the dispensing nozzle. Preferably, this distance is at most 10 mm, more preferably at most 5 mm. In a preferred embodiment, the negative electrode extends of from 2 mm to 4 mm from the positive electrode, whereby the latter most preferably is at the exit of the nozzle.

In an interesting embodiment, a portion of an extending electrode is insulated, such as to leave only a terminal length thereof not insulated. I.e., at the side of the dispensing nozzle, the extending electrode is insulated, and at the side serving to reach into the mouth, the electrode is not insulated. As an example, an embodiment is referred to whereby the first (negative) electrode extends 3 mm from the dispensing nozzle, having only the final, e.g., 1.5 mm not insulated. This leaves, in this example, a 1.5 mm distance insulated. It will be understood that around the insulated part of the electrode no hydroxide ions are generated. The inner surface of the nozzle is, for example, the positive electrode. This serves to keep the hydroxide ions away from the nozzle exit. Moreover, the protons formed at the positive electrode are thus far enough away from the gelling location (at 1.5 to 3 mm distance).

In an interesting embodiment, if a gelable composition is to be delivered to a plurality of locations on teeth or gums, the gelable composition present inside the nozzle after the administration of a first portion to a first location, is removed prior to the administration of a second portion of gelable composition to a second location. This has the advantage of avoiding a portion of more acidified liquid composition to be applied to teeth or gums, as changing the pH thereof would require more hydroxide ions generation, as a result of which gelling time would be longer.

The electrodes can be made of any suitable material, such as iron, carbon, platinum or any other electrical conductor material. In the invention it is preferred to use porous carbon, particularly for the anode (i.e., the second electrode) as such electrodes suppress the formation of protons, thus allowing the pH of the aqueous liquid substance to increase more efficiently.

The device of the invention is used to dispense an aqueous liquid substance and apply it on teeth or gums. It will be understood that the aqueous nature of the composition is a requirement for the electrochemical formation of hydroxide ions and protons.

The aqueous liquid substance is an oral care composition comprising at least one oral care agent comprised in a carrier that is gelable under the influence of a pH change. The oral care composition can be provided separately. I.e., typically an end-user of the device of the invention will obtain said composition off the shelf, and use it with the device of the invention. However, the oral care composition can also be comprised in a kit, together with the application device, or be part of the device.

Desirably, the oral care composition is sufficiently viscous to not flow away when applied on/between the teeth. Typically suitable viscosities are similar to the viscosities of toothpaste, e.g. about 500,000 mPa s). Generally, the viscosity will be higher than 10000 mPa s (10000 centiPoise). A preferred range is 50,000 to 1,000,000 cP.

Preferably, the device further comprises a container holding said aqueous liquid substance, or capable of being filled with said substance. This can be a separate container, it can be a cartridge removably attached to the dispensing unit, but it can also be an integral part, e.g. a liquid reservoir, of the dispensing unit.

Preferred gel compositions for use with the electrochemical pH increase of the invention are gels made of polysaccharide, particularly chitosan. Chitosan is known to be mucoadhesive. This is an advantage for the invention, as it adds to the retention oral care active agents comprised in the gel.

Suitable mucoadhesive gels are described, e.g., in Fini et al., Pharmaceutics 2011, 3, 665-679. Other adhesive composition can also be used. Reference is made, e.g., to US 2007/258916, wherein dental compositions are described that are given a high viscosity for better adherence to teeth. Also, a phosphoric acid gel carrier is described that serves to further improve retention on dentin surfaces. It will be appreciated that the skilled person is well aware of various different oral care compositions designed to deliver active agents locally to the teeth, and which will benefit from the possibility of the invention to have gelling be brought about by means of a pH increase.

The present invention provides the insight that pH-affected gelling or oral care compositions can be advantageously brought about, after application of the composition on gums or teeth, by applying an electrical potential difference. To this end, one aspect of the invention concerns a method of gelling a liquid composition suitable for application on teeth or gums and gelable by increasing the pH thereof, whereby the gelling is conducted by subjecting the liquid composition to an electrical potential difference of 1.5 to 10V when the composition has been applied on teeth or gums.

The gelable liquid used with the present invention serves as a carrier to administer one or more oral care agents to the teeth and/or gums.

The oral care agents comprised in the gelable liquid are preferably selected from the group consisting of anti-inflammatory agents, antiplaque agents, anti-tartar agents, anti-gingivitis agents, anti-bacterial agents, anti-caries agents, and combinations thereof.

A preferred anti-caries agent is fluoride. Suitable fluoride sources include sodium fluoride, stannous fluoride, sodium monofluorophosphate, zinc ammonium fluoride, tin ammonium fluoride, calcium fluoride, cobalt ammonium fluoride potassium fluoride, lithium fluoride, ammonium fluoride, zinc ammonium fluoride, tin ammonium fluoride, calcium fluoride, cobalt ammonium fluoride, water soluble amine hydrofluorides, or mixtures thereof. The fluoride is preferably present in an amount of at least 0.001%, more preferably, from 0.01 to 12%, and most preferably, from 0.1 to 5% by weight of the total liquid applied into the oral cavity.

Other possible oral healthcare active agents that can be included in the liquid are, e.g., antibacterial agents. These include, for example, phenolics and salicylamides, and sources of certain metal ions such as zinc, copper, silver and stannous ions, for example in salt form such as zinc, copper and stannous chloride, and silver nitrate. These are present in art-known small quantities when used. Typical oral care agents in common usage are chlorhexidine digluconate, cetylpyridinium chloride, stannous fluoride, sodium fluoride, hydrogen peroxide, zinc citrate, benzethonium chloride, zinc lactate, phenolic compounds (e.g., thymol, menthol, eucalyptol), triclosan, herbal extracts (e.g. sanguinarine).

Preferably, the device and method of the invention are applied for the purpose of removing bio film from teeth. To this end, an aspect of the invention concerns a method for cleaning dental plaque bio film from teeth, comprising the following steps:

applying a liquid gelable composition to the teeth, the composition having a viscosity such that substantially all exposed areas of the teeth are coverable by the liquid composition;

gelling the liquid composition on the teeth to produce a gel layer by increasing the pH of the liquid composition; therein the gel layer adheres more strongly to the dental plaque bio film than the bio film adheres to the teeth for example by means of strong electrostatic interactions when using a positively charged gel polymers, since the bio film surface has a net negative surface charge;

removing the gel layer from the teeth, and the dental plaque bio film along with the gel layer, wherein the dental plaque bio film adheres to the gel layer, wherein said increasing of the pH is conducted by subjecting the liquid composition to an electrical potential difference of 1.5 to 10 V.

Liquid compositions that are gelable by means of a pH change are generally known to the skilled person. The liquid generally comprises a solution or dispersion of a polymer. The most common polymer types are:

Acryl and vinyl polymers: cross linked acrylic acid-based polymers present swellable behavior in aqueous solutions due to the presence of ionizable functional groups. Under certain pH they acquire charge and the electrostatic repulsion between these groups favors the intake of water and the expulsion of the agent. This feature makes them suitable candidates for pH-triggered controlled release, at specific sites. Some of these polymers are commercialized under the names Carbopol®. E.g., a gelling system is known comprising 0.4% w/v carbopol/0.5% w/v chitosan which is in liquid state at room temperature and at a pH of 6, whilst it will undergo rapid transition into a viscous gel phase at a pH of above 7 (the system being known from ophthalmic use, with lacrimal fluid having a pH of 7.4).

Lactic and glycolic acid-based polymers show excellent biocompatibility and hydrophilic nature, which makes them good choices for controlled release and drug delivery.

Polysaccharides such as chitosan and its derivatives are water soluble, non-toxic, biocompatible and biodegradable. They, and their combination with poly (acrylic acid) or poly (methyl methacrylate), are mostly used to produce cross linked micro and nanoparticles for controlled release of proteins, vaccines, pharmaceutical compounds and pesticides.

Cellulose-derived polymers, which present different hydrophilicity, swelling and degradation behavior, also offer a flexible and tunable alternative for controlled release. Commercial examples of these materials are ETHOCEL™, METHOCEL™ and POLYOX™.

Poly (β-amino ester) polymers are also used to design pH-responsive polymer microspheres. Such systems degrade slowly at pH 7.4 but enable a fast and quantitative release (up to 90% of the encapsulated agent) in acidic conditions, which is of interest in biomedical applications to achieve specific different release rates within the physiological pH of the specific site. In the present invention this could be used for the release of crosslinkers, such as calcium ions, to trigger gelation of suitable gelling systems, such as based on alginates or carrageenan.

Mixed inorganic-organic polymers: silicones (siloxanes); hereby typically under alkaline conditions the material will be a colloidal solution, whilst under acidic conditions a three-dimensional gel network will form.

Liquid compositions that are capable of gelation under the influence of ions (i.e., by ionotropic gelation) are known to the skilled person. Ionotropic gelation is based on the ability of polyelectrolytes to cross link in the presence of counter ions to form hydrogels. The hydrogels are generally produced when a polymeric solution of a suitable polyelectrolyte is contacted with an aqueous solution of polyvalent cations. Typical polyelectrolytes are sodium alginate, gellan gum, carrageenan, carboxy methyl cellulose, pectin. Typical counter ions are multivalent metal salt solutions, such as calcium chloride solution.

High methoxyl pectin (HM) pectin is a known modified pectin that will form a gel at an acidic pH of 2.0 to 3.8, at a soluble solids content of at least 65%. Low methoxyl (LM) pectin forms gels in the presence of polyvalent cations, typically calcium (typically at least 15 mg Ca++/g pectin). LM pectin forms a gel over a wide range of pH, from 2.6 to 7.0, and with a soluble solid content between 10-70%.

It should be noted that several gelable compositions can be provided as either directly gelable by a pH change, or indirectly. In the event of a directly gelable composition, the composition comprises all of the required components to induce gel formation, but is not at the right pH. By changing the pH (increasing it in the event of, e.g., chitosan, or decreasing it in the event of, e.g., siloxanes or HM pectin) a gel will form. In the event of an indirectly gelable composition, typically such a composition satisfies its pH requirement for gelling, but lacks an essential reactive component for the gelation. This component, such as calcium ions in the event of, e.g., alginate, is then provided in a pH-sensitive carrier. The pH sensitive carrier, which can be a (nano)capsule, a liposome, a micelle, or another suitable particle, will comprise an aqueous metal salt solution providing the desired ions, upon releasing its content as a result of a pH change (typically a pH decrease).

The above-discussed device of the invention can also be comprised in an oral healthcare kit. Such a kit comprises a container having an oral care composition, said composition comprising at least one oral care agent comprised in a carrier that is gelable under the influence of a pH increase, and an applicator for said composition. The applicator thereby is a device as substantially described hereinbefore.

In an alternative embodiment, the container in the kit of the invention contains an oral care composition comprising at least one oral care agent, a substance such as alginate or carrageenan that will form a gel under the influence of ions (typically a polyelectrolyte), and a pH-sensitive carrier comprising such ions (typically polyvalent ions, particularly calcium ions).

In an interesting embodiment, the device of the invention is combined into a system further comprising a dental appliance for cleaning teeth, selected from the group consisting of electric toothbrushes, electric flossing devices, oral irrigators, and combinations thereof. Such dental appliances can be provided for various functions.

This typically refers to a toothbrush, preferably an electrical toothbrush, more preferably a sonic power toothbrush having a vibrating brush head. In such as toothbrush, the electrodes can be provided merely as an addition to the regular components of a toothbrush. These components generally are a housing part, which houses the necessary electronics and which usually is also the part held by the user, a generally replaceable brush part that on one longitudinal end has a releasable connection to one longitudinal end of the housing part, and that at the other longitudinal end contains a brush head comprising bristles, said head being capable of vibrating or rotating. In an embodiment of the invention, e.g., the first electrode (the electrode adapted to be held against the aqueous liquid composition at a location at or near teeth or gums), can be provided in the brush head, adjacent to the bristles thereof, and extending into substantially the same direction as the bristles. The second electrode, adapted to be held against the aqueous liquid composition at a location away from teeth or gums, can be positioned, e.g., halfway the length of the replaceable brush, or closer to the brush head. In this embodiment a gutter or a tube, or any other suitable duct, can be provided for dispensing the liquid aqueous composition. Said duct can be in fluid communication with a container for the liquid aqueous composition. The second electrode can be a part of such a duct made of an electrical conducting material, such as a metal electrode or a carbon electrode. The first electrode can be outside a dispensing nozzle that is in fluid communication with the duct, and particularly outwardly extending from such a nozzle into a direction that, upon usage, will be towards teeth or gums. In an interesting embodiment, the first electrode can be bristle comprised in the brush head. It will be understood that in such embodiment the second electrode will normally not be a bristle. In an embodiment wherein both electrodes are bristles comprised in the brush head, these must be of different length. The first electrode will then be a bristle of at least the same length as the majority of the other bristles. The second electrode must then be a bristle of shorter length, so as to avoid both electrodes from being in contact with the portion of the aqueous liquid composition that has been applied on teeth. The latter serves to avoid that the second electrode provides acid at a tooth surface and thereby would prevent gel formation, or reverse gel formation initially induced by the first electrode.

An electric flossing device, as is possibly comprised in the system of the invention, refers to such devices that serve to clean the interdental spaces generally by spraying air, by spraying liquid, or a combination thereof. In the system of the invention, such a device can also be of use in order to direct the oral care composition to the desired location in the oral cavity by the force of spraying.

It is noted that the gelling time available will depend on the type of dental appliance used. By way of guidance, typical available gelling times are 0.5 s to 1.5 s, typically 1 s, in the event of oral care agents applied in conjunction with an oral irrigator such as Philips AirFloss®. In the event of an electrical toothbrush, the available gelling time will generally be 2 s to 10 s, typically 5 s. It is also conceivable to combine the device of the invention into mouthguard systems. Since these concern appliances held in the mouth for some time, e.g. in professional dental whitening treatment, the gelling time can be longer, such as 0.5 minute to 1.5 minutes, typically 1 minute (60 s).

It is to be understood that the system can comprise its various parts as separate components, not packaged or provided together.

The invention will be further illustrated hereinafter with reference to the figures.

FIG. 1 shows a schematic top view of two teeth (1), separated by an interproximal space (2). An oral irrigator comprising a spray nozzle (3), and additionally provided with a dispensing nozzle (4) is brought to the interproximal space (2). A gel (5) is applied via said dispensing nozzle (4). The dispensing nozzle (4) comprises a negative electrode (6) that extends into the interproximal space (2), and a positive electrode (7) that is shorter, so as to not extend into the interproximal space. The negative electrode is configured in a substantially elongated shape extending substantially along an axis projecting outward from and through the dispensing nozzle (4), the negative electrode configured in a substantially elongated shape extending outward from and through the dispensing nozzle (4). The negative and positive electrodes (6) and (7), respectively, have proximal and distal ends. The proximal and distal ends of the positive electrode (7) are upstream of the distal end of the negative electrode (6).

Figure 2:
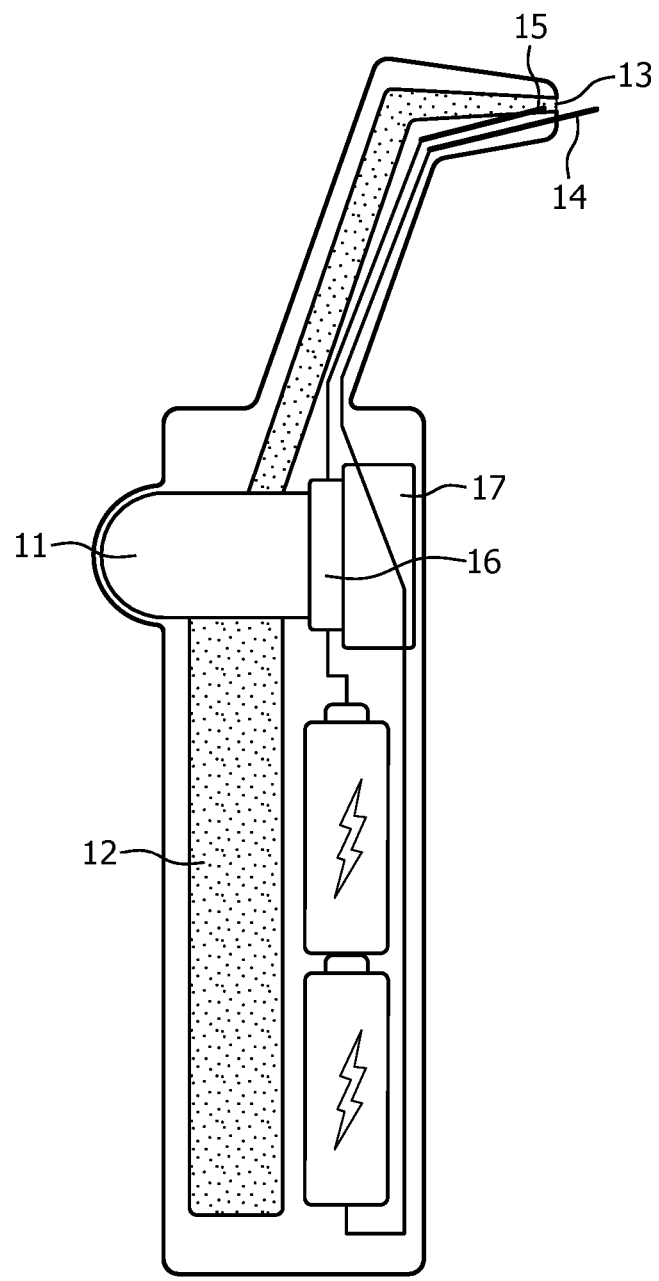
FIG. 2 is a schematic drawing of a device in accordance with the invention.

FIG. 2 shows a schematic representation of a possible stand-alone embodiment for application of gel locally. A thumb operated manual pump (11) can be employed to press a certain amount of gelable liquid inside for example an interproximal space. When the pump is released it relaxes and sucks up the liquid from a gelable liquid sachet (12), which fluid is then dispensed via a fluid nozzle exit (13). Such sachet systems and manually operated pumps are well known in the art, and are very suitable of delivering a viscous liquid, giving the user sufficient control over the amount of liquid deposited. The devices comprises a negative electrode (14) and a positive electrode (15). When pushing the pump an electrical switch (16) will also be activated, signalling to a controller unit (17) that the electrodes (14, 15) can be switched on. After a predetermined time, e.g. 1 to 5 s, the controller switches off the electrodes, and preferably signals the user with a sound that the device can be moved to the next location. The user may set the gel time himself, if he wishes to deposit more or less of the gel on the teeth, depending on the time he is willing to spend.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein a plurality of different agents is administered via a single gelable composition.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose a new method, and a system, for increasing the pH of a composition applied on teeth and/or gums. The composition is gelable under the influence of a pH change. The pH change typically is a pH increase in the event of a direct pH-triggered gelation. The pH change typically is a pH decrease in the event of gelation induced by ions, such as calcium ions, released from a pH-sensitive carrier. The device comprises a dispensing unit for the composition, a distal end of which is adapted to apply said substance onto teeth or gums. The device further comprises an electrode system comprising first and second electrodes, the first electrode being adapted to be held against the composition at a location at or near teeth or gums, and the second electrode being adapted to be held against the composition at a location away from teeth or gums, The electrode system is adapted so as to provide an electrical potential difference of 1.5 to 10 Volt between the electrodes.

The invention claimed is:

1. A device for the application on teeth or gums of an aqueous liquid oral care composition that is gelable under the influence of a change in pH, and changing the pH of said composition when the composition has been applied on teeth or gums; the device comprising an applicator for said composition, a distal end of which comprises a dispensing nozzle to apply said composition onto teeth or gums, and an electrode system comprising first and second electrodes integrated with the applicator, the first electrode configured in a substantially elongated shape extending substantially along an axis projecting outward from and through the dispensing nozzle, the first electrode arranged within and extending from the distal end of the applicator and the second electrode being arranged entirely within the applicator, the second electrode having proximal and distal ends that are both upstream of a distal end of the first electrode; the electrode system being adapted so as to provide an electrical potential difference of 1.5 to 10 Volt between the electrodes, such that upon providing said potential difference to the applied composition, hydroxide ions (OH−) form at one electrode, and protons (H+) form at the other electrode, in order to bring about gelation of said composition.

2. A device according to claim 1, wherein a first direction of the electrical potential difference is such that hydroxide ions (OH−) form at the first electrode, and protons (H+) form at the second electrode.

3. A device according to claim 2, wherein a second direction of the electrical potential difference is such that hydroxide ions (OH−) form at the second electrode, and protons (H+) form at the first electrode.

4. A device according to claim 1, wherein the second electrode is at or proximate to the distal end of the applicator yet not extending from said distal end.

5. A device according to claim 1, wherein the second electrode is comprised in a wall of the applicator.

6. A device according to claim 4, wherein the second electrode is a positive electrode positioned at the exit of the dispensing nozzle, and the first electrode is a negative electrode extending 1 to 10 mm from the exit of the dispensing nozzle.

7. A device according to claim 1, wherein the device further comprises a dental appliance for cleaning teeth selected from the group consisting of electric toothbrushes, electric flossing devices, oral irrigators, and combinations thereof.

8. A method of gelling a liquid composition suitable for application on teeth or gums and gelable by increasing the pH thereof, whereby the gelling is conducted by subjecting the liquid composition to an electrical potential difference of 1.5 to 10V when the composition has been applied on teeth or gums, and wherein the electrical potential different is applied by means of the device according to claim 1.

9. A method according to claim 8, wherein the gelable composition comprises chitosan.

10. An oral healthcare kit comprising a container having an oral care composition, said composition comprising at least one oral care agent comprised in a carrier that is gelable under the influence of a pH increase, and an applicator for said composition, wherein the applicator is a device comprising a dispenser for said composition, a distal end of which is adapted to apply said composition onto teeth or gums, and an electrode system comprising first and second electrodes, the first electrode being adapted to be held against the aqueous liquid composition at a location at or near teeth or gums, and the second electrode being adapted to be held against the aqueous liquid composition at a location away from teeth or gums; the electrode system being adapted so as to provide an electrical potential difference of 1.5 to 10 Volt between the electrodes, such that upon providing said potential difference to the applied composition, hydroxide ions (OH−) form at one electrode, and protons (H+) form at the other electrode, in order to bring about gelation of said composition, the device being according to claim 1.

11. A kit according to claim 10, wherein the gelable composition comprises chitosan.

12. An oral healthcare kit comprising a container having an oral care composition, said composition comprising at least one oral care agent, a substance capable of forming a gel under the influence of metal ions, and a pH-sensitive carrier comprising such metal ions, the kit further comprising an applicator for said composition, wherein the applicator is a device comprising a dispenser for said composition, a distal end of which is adapted to apply said composition onto teeth or gums, and an electrode system comprising first and second electrodes, the first electrode being adapted to be held against the aqueous liquid composition at a location at or near teeth or gums, and the second electrode being adapted to be held against the aqueous liquid composition at a location away from teeth or gums; the electrode system being adapted so as to provide an electrical potential difference of 1.5 to 10 Volt between the electrodes, such that upon providing said potential difference to the applied composition, hydroxide ions (OH−) form at one electrode, and protons (H+) form at the other electrode, in order to bring about gelation of said composition, the device being according to claim 1.

13. A kit according to claim 12, wherein the gel-forming substance is selected from alginate, carrageenan, and mixtures thereof, and the metal ions comprise calcium ions.

14. A kit according to claim 10, wherein the oral care agent is selected from the group consisting of dentifrices, antiplaque compositions, anti-tartar compositions, anti-gingivitis compositions, anti-caries compositions, anti-bacterial compositions, compositions for periodontal treatment, and combinations thereof.

\* \* \* \* \*